United States Patent
Kumari et al.

(10) Patent No.: US 11,858,899 B2
(45) Date of Patent: Jan. 2, 2024

(54) COMPLEXATION OF PIRFENIDONE WITH POLYPHENOLIC CALIXARENE OR RESORCIN[4]ARENES

(71) Applicant: University of Cincinnati, Cincinnati, OH (US)

(72) Inventors: Harshita Kumari, Loveland, OH (US); Suchitra Panigrahi, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 67 days.

(21) Appl. No.: 17/837,700

(22) Filed: Jun. 10, 2022

(65) Prior Publication Data

US 2023/0116697 A1    Apr. 13, 2023

Related U.S. Application Data

(60) Provisional application No. 63/289,298, filed on Dec. 14, 2021, provisional application No. 63/209,332, filed on Jun. 10, 2021.

(51) Int. Cl.
*C07D 213/64* (2006.01)
*C07C 35/44* (2006.01)

(52) U.S. Cl.
CPC .......... *C07D 213/64* (2013.01); *C07C 35/44* (2013.01); *C07B 2200/13* (2013.01)

(58) Field of Classification Search
CPC ... C07D 213/64; C07C 35/44; C07B 2200/13; A61P 17/10
See application file for complete search history.

(56) References Cited

U.S. PATENT DOCUMENTS 9,182,666 B2 * 11/2015 Echigo .................... C07C 67/14
2018/0009753 A1 * 1/2018 Razzetti ............... C07D 213/64

* cited by examiner

*Primary Examiner* — Sikarl A Witherspoon
(74) *Attorney, Agent, or Firm* — Brent M. Peebles

(57) ABSTRACT

A cocrystal complex of pirfenidone with a polyphenolic macrocycle host is disclosed. The composition is useful, in some embodiments, as an acne treatment. In one embodiment, the macrocycle is calixarene or a calixarene derivative. In another embodiment, the macrocycle is resorcin[4]arene. In one embodiment, the macrocycle is C-methylresorcin[4]arene (RsC1). In another embodiment, the macrocycle is C-butylresorcin[4]arene (RsC4).

15 Claims, 10 Drawing Sheets

COMPLEXATION OF PIRFENIDONE WITH POLYPHENOLIC CALIXARENE OR RESORCIN[4]ARENES

CROSS REFERENCE TO RELATED APPLICATIONS

This application claims priority to U.S. Provisional Application Ser. No. 63/209,332, filed Jun. 10, 2021, and U.S. Provisional Application Ser. No. 63/289,298, filed Dec. 14, 2021, which applications are hereby incorporated by reference in their entirety.

TECHNICAL FIELD

The present invention relates to supramolecular assemblies that are useful for treating acne type skin conditions.

BACKGROUND OF THE INVENTION

Acne vulgaris is a complex skin disorder involving multiple abnormalities of the pilosebaceous unit. Acne is doubtless the most frequent skin disease worldwide during puberty and worsens throughout adolescence. Acne occurs mostly in the face, forehead, cheek and nasolabial fold, next in chest, back and shoulder. Usually, the skin damage caused by acne does not have a subjective symptom. Pain may be accompanied under severe inflammation reactions. Acne can be classified into acne, papule, pustule and nodular cyst. Acne affects 80-90% of teenagers. After adolescence, acnes often can be abated automatically or cured, except that acne persists in some patients into their thirties. Although acne has a tendency of self-healing, the acnes themselves and scars caused by the acnes without timely treatment may severely affect the life quality of the patient and cause mental pressure and financial burden on patients.

Currently, commonly used acne-removing products in the market use salicylic acid, capryloyl salicylic acid, ethanol, fruit acid and the like as the main active ingredients for disinfection and anti-inflammation, avoiding formation of inflammatory acne. However, these ingredients produce relatively high irritation and often cause side-effects such as skin sensitivity and sharp pain. Other traditional acne treatments include combination therapies of antibiotics and anti-inflammatory agents. However, these often lead to severe side effects and discontinuation of therapy along with the development of antibiotic resistance. Therefore, a need still exists for new effective acne treatments that avoid antibiotic resistance.

SUMMARY OF THE INVENTION

In one embodiment, the present invention addresses that need with a composition that includes a cocrystal complex of pirfenidone with a polyphenolic macrocycle host. The composition is useful, in some embodiments, as an acne treatment. In one embodiment, the macrocycle is calixarene or a calixarene derivative. In another embodiment, the macrocycle is resorcin[4]arene. In one embodiment, the macrocycle is C-methylresorcin[4]arene (RsC1). In another embodiment, the macrocycle is C-butylresorcin[4]arene (RsC4). In yet another embodiment, the cocrystal complex includes pirfenidone with a resorcin[4]arene macrocycle with two different tail lengths.

In another embodiment, an antibacterial composition is disclosed that includes a cocrystal complex of pirfenidone with a polyphenolic resorcin[4]arene or calixarene macrocycle. In one embodiment, the cocrystal complex is from about 4 to about 8% by weight of the antibacterial composition. In another embodiment, the antibacterial composition also includes a cosmetically acceptable carrier. In one embodiment, the carrier includes one or more carriers selected from the group consisting of preservatives, emollients, emulsifying agents, surfactants, moisturizers, gelling agents, thickening agents, conditioning agents, film-forming agents, stabilizing agents, anti-oxidants, texturizing agents, gloss agents, mattifying agents, solubilizers, pigments, dyes, and fragrances.

In another embodiment of the present invention, a method of treating a subject to prevent, treat or reverse acne or post-acne lesions is provided. The method involves applying a therapeutically effective amount of a composition that includes a cocrystal complex of pirfenidone with a polyphenolic macrocycle host to the skin of a subject in need of such treatment. In one embodiment, the method involves applying a therapeutically effective amount of a composition that includes a cocrystal complex of pirfenidone with a polyphenolic resorcin[4]arene macrocycle host to the skin of a subject in need of such treatment. In another embodiment, the method involves applying a therapeutically effective amount of a composition that includes a cocrystal complex of pirfenidone with a polyphenolic calixarene derivative macrocycle host to the skin of a subject in need of such treatment.

BRIEF DESCRIPTION OF THE DRAWINGS

The foregoing summary, as well as the following detailed description of preferred embodiments of the application, will be better understood when read in conjunction with the appended drawings.

DETAILED DESCRIPTION

Figure 1A:
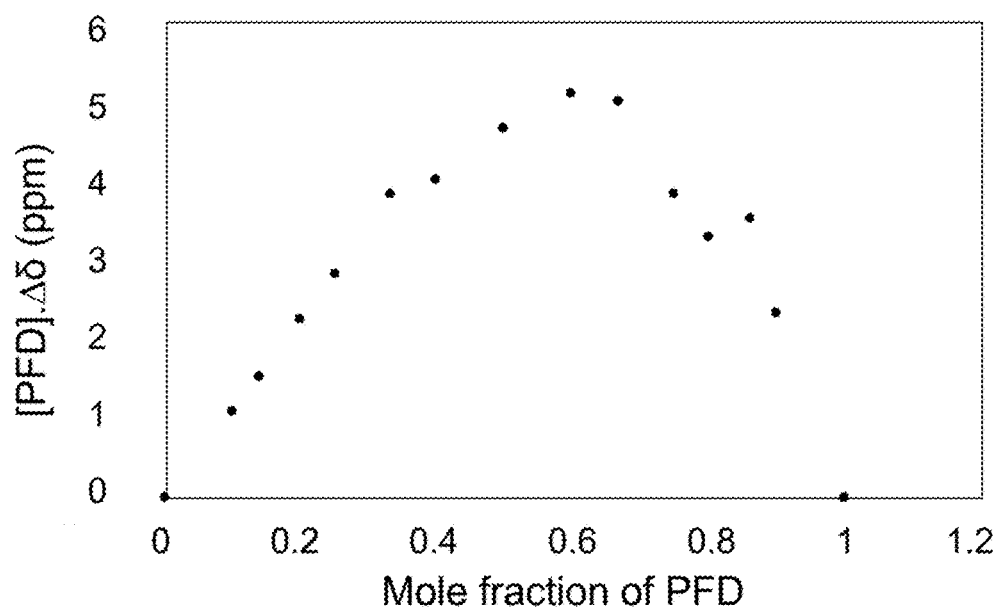
FIG. 1A is a graph showing a Job's plot constructed from the chemical shift change ($\Delta\delta$) of the phenyl ring protons (#2) of PFD in $^1$H NMR spectra by varying the ratio between PFD and RsC4.

One skilled in the art will recognize that the various embodiments may be practiced without one or more of the specific details described herein, or with other replacement and/or additional methods, materials, or components. In other instances, well-known structures, materials, or operations are not shown or described in detail herein to avoid obscuring aspects of various embodiments of the invention. Similarly, for purposes of explanation, specific numbers, materials, and configurations are set forth herein in order to provide a thorough understanding of the invention. Furthermore, it is understood that the various embodiments shown in the figures are illustrative representations and are not necessarily drawn to scale.

Reference throughout this specification to "one embodiment" or "an embodiment" means that a particular feature, structure, material, or characteristic described in connection with the embodiment is included in at least one embodiment of the invention, but does not denote that they are present in every embodiment. Thus, the appearances of the phrases "in an embodiment" or "in another embodiment" in various places throughout this specification are not necessarily referring to the same embodiment of the invention. Further, "a component" may be representative of one or more components and, thus, may be used herein to mean "at least one."

The term "therapeutically effective amount" means an amount of a compound according to the disclosure which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the disclosure which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the disclosure, and the age, body weight, general health, sex, and diet of the patient. Such a therapeutically effective amount can be determined routinely by one of ordinary skill in the art having regard to their own knowledge, the prior art, and this disclosure.

The present invention relates generally to the complexation of a supramolecular host and guest cocrystal to form a supramolecular assembly. Supramolecular assemblies are generally described as inclusion/host-guest complexes comprised of two or more molecules which bind through non-covalent interactions. In one embodiment, the present invention involves the application of these complexes as supramolecular drugs in the pharmaceutical/cosmetic sciences.

To develop a microbiologically potent supramolecular drug, the present invention complexes a macrocyclic host with a guest molecule, such as an NSAID. Non-steroidal anti-inflammatory drugs (NSAIDs) are widely used to treat inflammation, pain, and fever that are associated with bacterial infections. Pirfenidone (5-methyl-1-phenylpyridin-2-one) ("PFD"), an FDA-approved antifibrotic drug used for the treatment of idiopathic pulmonary fibrosis, is also an NSAID. The presence of an anti-bacterial pyridone nucleus, which is found in broad-spectrum fluoroquinolone antibiotics, along with recent studies showing NSAIDs might have antibacterial properties, indicates the potential utility of PFD.

An example of the supramolecular assemblies of the present invention are assemblies which contains polyphenolic resorcin[4]arenes as host and pirfenidone for skin conditions such as acne. In another embodiment, calixarene is used as the host with pirfenidone. These assemblies have advantages over other conventional therapies recommended for the treatment of acne vulgaris. These novel 1:1 cocrystal complexes have the potential to overcome the drawbacks and complexity of multiple therapies in acne by providing clinical benefits needed, all in one. These new cocrystals can be used as anti-fibrotic, anti-inflammatory, antioxidant and antimicrobial agents in the prevention, treatment and reversal of acne and post-acne lesions. Through the medical application of the pirfenidone, the formation of skin scars can be inhibited. It can also be used to reduce the redness/inflammation of the skin, whereas resorcin[4]arenes can be used as free radical scavenger to halt the formation of new acne breakouts, and to help repair acne skin.

Pirfenidone

Figure 2A:
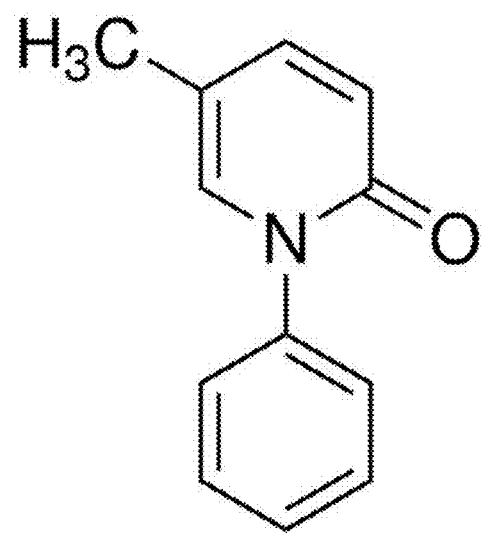
FIG. 2A is image showing the chemical structure of pirfenidone (PFD).

Pirfenidone (5-methyl-1-phenylpyridin-2-one), a pyridone derivative, is an FDA-approved pharmaceutical active (see FIG. 2A). It is a new drug molecule with antifibrotic and anti-inflammatory effects utilized to treat idiopathic lung fibrosis. It is commercially accessible in the market under the brand name of ESBRIET. Pirfenidone (PFD) shows antifibrotic effect through multiple mechanisms, including attenuation of fibroblast proliferation, differentiation, and related collagen synthesis and regulation of fibrotic growth factors and cytokines. More specifically, it modulates diverse cytokines action, involving TGF-, TNF-, epidermal growth factor, platelet-derived growth factor, VEGF, IGF-1, fibroblast growth factor, interferon-, interleukin (IL)-1, IL-6, and IL-8 and it has shown promising effects in vitro and in vivo settings. Results showed it acts on both the inflammatory and the fibrotic phases. Clinical features of acne include seborrhoea, prevalence of acne bacteria, non-inflammatory lesions, inflammatory lesions and various degrees of scarring. The deep nodular acne lesions are difficult to treat and remain even after acne is treated. So, the present invention should treat post acne lesions based on in vitro and in vivo effects reported in literature for PFD. In addition, the polyphenolic host provide antioxidant effect by reducing oxidative stress which is leading cause of acne breakouts.

These beneficial effects of PFD could lead to treatment for other skin diseases/conditions, such as scleroderma, acne, hypertrophic scars. However, PFD is accompanied by elevated liver enzyme levels and severe dermatological and gastrointestinal adverse effects, particularly phototoxicity and skin rash. These side effects have hindered using the medication as a potential topical agent for different skin diseases/conditions. In order to lessen the effects of PFD-induced phototoxicity, it is generally recommended to avoid exposure to sunlight by using photoprotective clothing and sunscreens.

The present invention takes an alternative way to protect the photosensitive PFD by complexing with a polyphenolic host. We have found that a chemical or conformational perturbation from a host molecule can influence the mechanism of PFD action, which in turn alters its clinical behavior and associated side effects. The present invention discloses the first cocrystal structure of the PFD with RsCx macrocycle with two different tail lengths.

In one embodiment, the present invention assembles a resorcin[4]arene-based drug cocrystal with PFD, in which part of the macrocycle is not just acting as a drug carrier. However, the macrocycle chemistry potentially highlights a noticeable effect on the clinical behavior of the drug molecule. Also, polyphenolic resorcin[4]arenes have anti-bacterial properties, which can be beneficial in treating acne bacteria.

Resorcinol

Resorcinol[4]arenes represent a class of cyclic polyphenolic compounds obtained from the condensation reaction of resorcinol with several aldehydes in acidic solutions. Interestingly, the flexibility in changes of electron-rich upper-rim bunches and lower-rim alkyl chains with distinctive substituents driven to a wide assortment of tunable host molecules. Amidst cyclic polyphenolic cavitands, resorcinarenes have broadly been inspected in host-guest chemistry due to their conical shape to develop valuable (bio)materials and sensors. A variety of guests, from cationic to neutral molecules, have been found to embed into this cavity, through C—H . . . π, cation . . . π and π . . . π interactions. This ability to act as a host, together with its adaptability and affinity towards hydrogen bonding, makes resorcinol[4] arenes a perfect candidate for cocrystallizations. Despite enjoying omnipresent investigation in chemical studies, cyclic polyphenol-based host-guest chemistry including pharmaceutical actives is undoubtedly in its earliest stages.

Figure 2B:
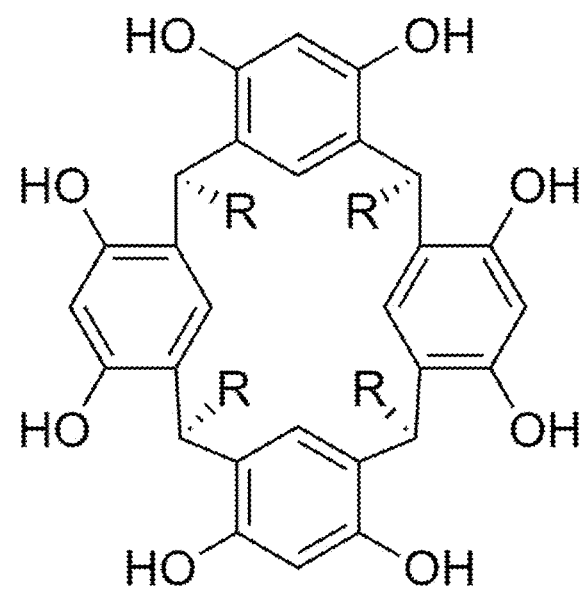
FIG. 2B is an image showing the chemical structure of C-methylresorcin[4]arene (RsC1).
Figure 2C:
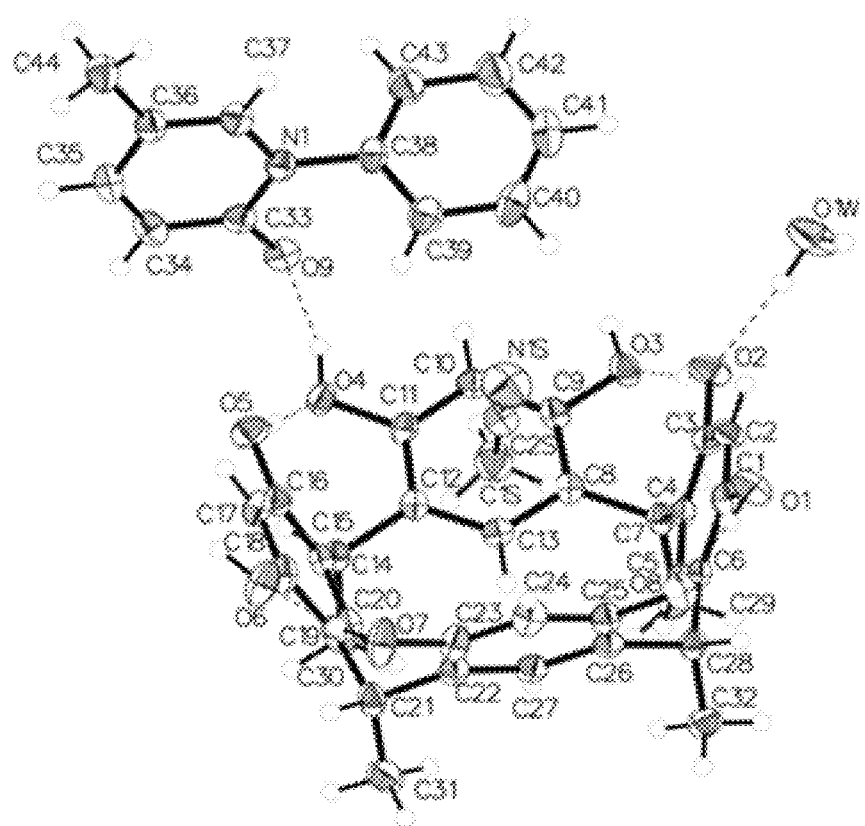
FIG. 2C is a chemical structure for RsC1-PFD (1:1) Cocrystal (C46H48 N2 O10).

The present invention uses cyclic poplyphenols like resorcinol[4] for cocrystallization with phototoxic drugs due to their potential to protect chemical induced ROS generation based on the polphenolic antioxidant activity. One objective of the present invention is to generate a cocrystal complex of PFD with a polyphenolic macrocycle host through non-covalent supramolecular interactions for treating acne type skin conditions. One embodiment of the present invention uses RsC1, which is antibacterial in nature. The complex has both anti-acne and anti-bacterial applications. The chemical structure of C-methylresorcin[4]arene (RsC1) is shown in FIG. 2B. The chemical structure for RsC1-PFD (1:1) Cocrystal ($C_{46}H_{48}N_2O_{10}$) is shown in FIG. 2C. In another embodiment, C-butylresorcin[4]arene (RsC4) is used.

Calixarene

The field of supramolecular chemistry has engaged in relentless development for several years, in which macrocyclic cavitands are crucial units. Familiar illustrations of such synthetic supramolecular cavitands incorporate cyclodextrins, calixarenes and analogs, pillarenes, and cucurbiturils. These cavitands basically contrast in symmetry, shape, and hydrophilicity. Among other macrocycles, the family of macrocycles known as calixarenes has held particular importance due to their bowl-shaped conformation. They are considered to be the model for host-guest binding and self-assembly. Calixarenes are phenol-based macrocycles, whereas their sister derivatives (resorcinarenes and pyrogalloarene) are synthetic polyphenols. The calixarene molecules may be characterized as calix(N)arenes in which N is an integer within the range of 4-8. Thus the calixarenes ranging from calix(4)arene to calix(8)arene and their derivatives can be employed in carrying out the invention. The calixarene molecules may be distally substituted with a substituent selected from the group consisting of methyl, ethyl, propyl, butyl amyl or phenyl groups.

Cocrystal

The present inventive cocrystal of host and guest is moderately lipophilic in nature based on molecular structure. The lipophilic nature helps in skin permeation for localized effect as required in treating acne topically. Chemically, they are linked by non-covalent bond which helps in dissociation and providing individual biological effects such as antioxidant, anti-inflammatory, anti-bacterial and anti-scarring.

The cocrystals of the present invention can be included in a number of formulations, including formulations for the treatment of acne and antibacterial formulations. In an embodiment, a formulation for use according to the invention is suitable for topical or local application to the skin, in particular human skin. The ingredients are combined with a "cosmetically-acceptable topical carrier," i.e., a carrier for topical use that is capable of having the other ingredients dispersed or dissolved therein, and possessing acceptable properties rendering it safe to use topically. A formulation which is "suitable for" topical or local application may also be adapted for topical or local application.

A formulation for use according to the invention may be in the form of a fluid, for example a lotion, cream, ointment, varnish, foam, paste, gel or other viscous or semi-viscous fluid, or a less viscous fluid such as might be used in sprays or aerosols. It may take the form of a solution, suspension or emulsion. It may take the form of a powder or of granules, which may be designed to be added to liquid (e.g. water) prior to use.

In an embodiment the formulation is, or may be, applied to a substrate such as a sponge, swab, brush, pad, tissue, cloth, wipe, skin patch or dressing (which includes a bandage, plaster, skin adhesive or other material designed for application to a tissue surface), to facilitate its administration.

For use in the treatment of acne, the formulation may for example take the form of a lotion, cream, ointment, varnish, foam, paste or gel or it may be, or be capable of being, applied to a substrate of the type described above. The compositions of the present invention may be prepared using methodology that is well known by an artisan of ordinary skill in the field of cosmetics formulation.

The cocrystals of the present invention may be included in formulations at various concentrations, depending on the specific end use and carrier. In one embodiment, the cocrystals comprise from about 2 to about 10 wt % of a formulation. In another embodiment, the cocrystals comprise from about 4 to about 8 wt % of a formulation.

In the examples below, host-guest complexation was studied: spectroscopy (solution mix) and crystallography (solvent evaporation in solid-state) techniques using NMR, UV-vis and X-ray to identify the stoichiometry and in-vitro anti-bacterial studies. It was found that the complex between PFD-RsC1 were held together by hydrogen-bonding and hydrophobic interactions and exhibits a superior behavior over the drug alone by improving the MIC value against Gram-positive and negative bacteria. The present invention is useful in a variety of applications, including skin care applications for acne vulgaris via a single treatment. The present invention may also decrease resistance associated with antibiotics use for treatment. The RsC1-PFD complex of the present invention may also be useful on acne bacteria (*Propionibacterium acnes*).

EXAMPLES

Example 1

The following 1H NMR and diffusion ordered NMR (DOSY) results were found for PFD, RSC4 and RSC4:PFD (1:1 and 2:1). All samples were dissolved in d3-ACN. All the reagents and solvents involved in these examples were employed as purchased and used without further purification unless otherwise noted. All chemical shifts are reported in ppm with residual solvents or TMS (tetramethylsilane) as the internal standards. A saturated solution of PFD, RSC4 and individual guest with varying ratios of (RSC4:PFD, 1:1 and 2:1) was prepared in d3-ACN with an internal standard of 1 v/v % TMS for NMR measurements. The 1H-NMR spectra were obtained using a 400 MHz NMR spectrometer (Bruker AV-400). All experiments were done at 25° C. To minimize convection in DOSY measurement all samples were placed in 3 mm tubes and the Bruker pulse sequence named "ledbpgp2s" was used with Z gradient strength stepping from 5 to 95% (total 16 data points). The probe's maximum Z gradient strength was 53.5 G/cm. The diffusion delay (d20) was set to either 50 ms or 90 ms and the gradient pulse (p30) was set to 2.2 ms. Diffusion coefficient was obtained by fitting peak intensity as a function of gradient strength using Bruker supplied DOSY2D program. The reported diffusion coefficient was average of multiple experiments.

Example 2

Tests were conducted to check the antioxidant/antibacterial activity of macrocycle and host-guest compounds. 5 uL of 0.01M compound, 5 uL (premixed, 0.01M compound+ 1M Pyrogallol, 1:1) and 5 uL (premixed, 0.01M compound+ 0.88M H2O2, 1:1) were added on paper discs placed on plates. 5 uL of 1M pyrogallol, 5 uL of 0.88M H2O2 were used as control (oxidants).

TABLE 1

| Sample Code | Compound | Weight (mg) | Volume (mL) | Stock solution | Solvent |
|---|---|---|---|---|---|
| | | Stock Solution | | | |
| R1 | RsC1 | 5.44 | 1 | 0.01M | DMSO |
| D | PFD | 9.26 | 5 | 0.01M | DMSO |
| RD | RsC1-PFD (1:1) Cocrystal | 7.88 | 1 | 0.01M | DMSO |
| R4 | RsC4 | 7.12 | 1 | 0.01M | DMSO |
| P6 | PgC6 | 9.03 | 1 | 0.01M | DMSO |
| PR | P2R2C4 | 7.44 | 1 | 0.01M | DMSO |
| VK | VK-28 | 1 | 1 | 0.01M | DMSO |
| Py | Pyrogallol | 6.30 | 5 | 1M | Water |

Example 3

Figure 3A:
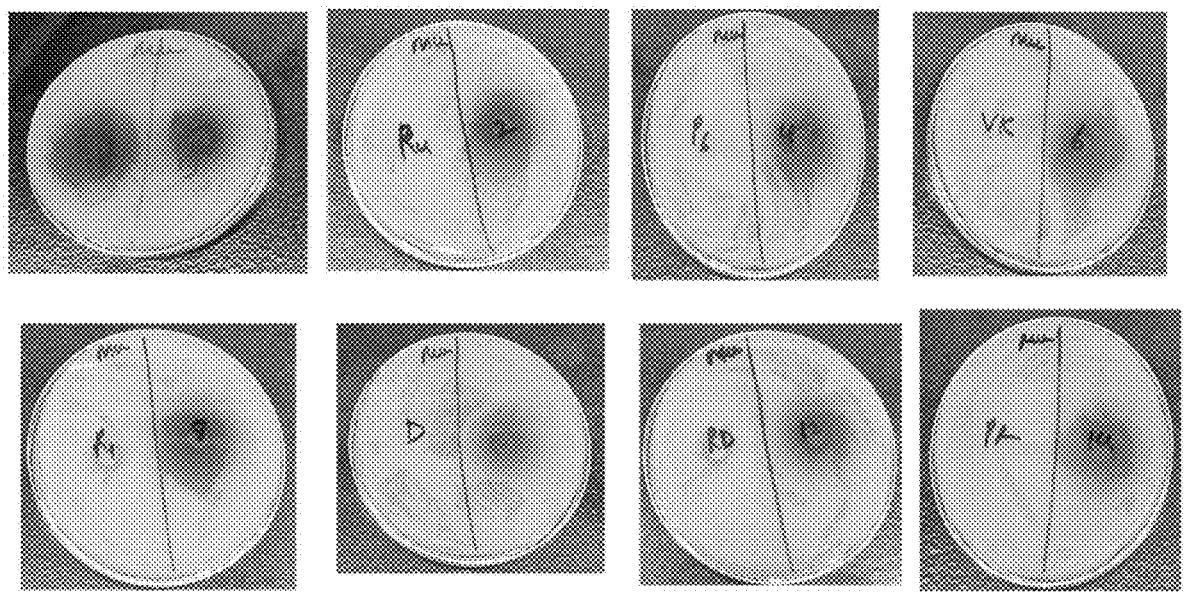
FIG. 3A is a series of images showing the zone of inhibition (ZI) for *Staphylococcus aureus* (G+ve) in presence of pure Pyrogallol, Pure compound and (Compound+Pyrogallol).
Figure 3B:
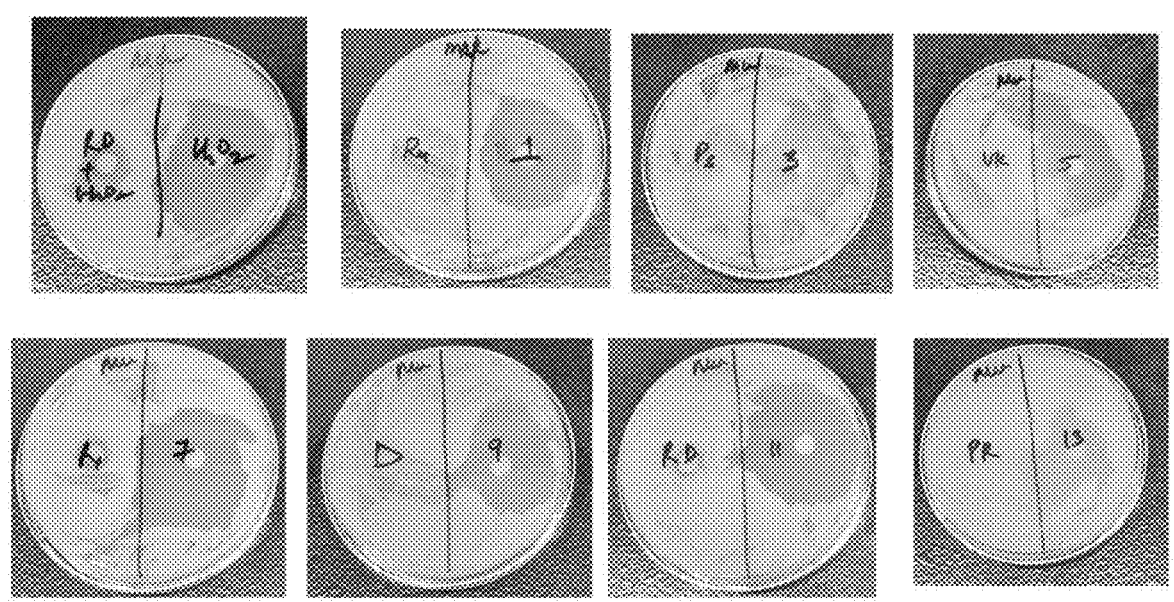
FIG. 3B is a series of images showing the zone of inhibition (ZI) for *Staphylococcus aureus* (G+ve) in presence of pure H2O2, pure compound and (Compound+H2O2).

In the following tables, Decrease/Increase means wrt pure H2O2 or pyrogallol. If ZI decreased (shrink) as compared to pyrogallol and H2O2, then they are having antioxidant activity, and if the zone increases then it is showing oxidant activity. If the pure compound shows ZI, then it means the compound has anti-bacterial activity. See FIGS. 3A and 3B. Zone=mm of zone width around disk.

TABLE 2

Observations w.r.t. Zone of inhibition (ZI) for *Staphylococcus aureus* (G + ve) bacteria

| Sample Code[a,b,c] | 5 uL of 0.01M Compound[a] | 5 uL of (Compound + H2O2)[b] | 5 uL of (Compound + Pyrogallol)[c] | 5 uL of 0.88M H2O2 | 5 uL of 1M pyrogallol | Inference |
|---|---|---|---|---|---|---|
| *R4, 1, 2 | No ZI | ZI decreased slightly (3.6 mm) | ZI decreased slightly (2.3 mm) | ZI (4.6 mm) | ZI (3.3 mm) | Low radical scavenger |
| P6, 3, 4 | No ZI | ZI decreased slightly (3.8 mm) | Noticeable decrease in ZI (2 mm) | ZI (4.6 mm) | ZI (3.3 mm) | Low radical scavenger |
| VK, 5, 6 | No ZI | ZI decreased slightly (3.7 mm) | ZI decreased slightly (2.3 mm) | ZI (4.6 mm) | ZI (3.3 mm) | Low radical scavenger |
| *R1, 7, 8 | Slight ZI (1.2 mm) | ZI decreased slightly (4.2 mm) | ZI decreased slightly (2.5 mm) | ZI (4.6 mm) | ZI (3.3 mm) | Anti-bacterial potential/Low radical scavenger |
| D, 9, 10 | No ZI | ZI decreased slightly (3.8 mm) | No ZI | ZI (4.6 mm) | ZI (3.3 mm) | Moderate radical scavenger |
| RD, 11, 12 | Slight ZI (1.1 mm) | Significant decrease in ZI (1.7 mm) | Noticeable decrease in ZI (1.8 mm) | ZI (4.6 mm) | ZI (3.3 mm) | Anti-bacterial potential/High radical scavenger |

TABLE 2-continued

Observations w.r.t. Zone of inhibition (ZI) for *Staphylococcus aureus* (G + ve) bacteria

| Sample Code[a,b,c] | 5 uL of 0.01M Compound[a] | 5 uL of (Compound + H2O2)[b] | 5 uL of (Compound + Pyrogallol)[c] | 5 uL of 0.88M H2O2 | 5 uL of 1M pyrogallol | Inference |
|---|---|---|---|---|---|---|
| PR, 13, 14 | No ZI | Noticeable decrease ZI (2.8 mm) | ZI decrease slightly (2.4 mm) | ZI (4.6 mm) | ZI (3.3 mm) | Moderate OH radical scavenger |

[a] represents compound
[b] represents 5 uL (premixed, 0.01M compound + 0.88M H2O2, 1:1)
[c] represents 5 uL (premixed, 0.01M compound + 1M Pyrogallol, 1:1)
*represents that both R1 and R4 compound has main structure but only differs in carbon tail length R1 is a macrocycle which is showing slight anti-bacterial activity against *Staphylococcus aureus* (G+ve) bacteria, but when complexed with D (i.e., RD) shows antibacterial as well as antioxidant activity. The drug itself shows low to high free radical scavenging effect in the presence of H2O2 and pyrogallol. R1 and R4 being the same molecule, only differing in tail length, has shown low anti-bacterial activity (R1) to none (R4) respectively.

TABLE 3

Observations w.r.t. Zone of inhibition (ZI) for *Pseudomonas aeruginosa* (G-ve) bacteria

| Sample Code[a,b,c] | 5 uL of 0.01M Compound[a] | 5 uL of (Compound + H2O2)[b] | 5 uL of (Compound + Pyrogallol)[c] | 5 uL of 0.88M H2O2 | 5 uL of 1M pyrogallol | Inference |
|---|---|---|---|---|---|---|
| *R4, 1, 2 | No ZI | ZI decreased slightly (2.1 mm) | Slight increase ZI (1.4 mm) | ZI (2.7 mm) | ZI (1.1 mm) | Low radical scavenger |
| P6, 3, 4 | No ZI | ZI decreased slightly (2.2 mm) | ZI is same as pyrogallol (1.2 mm) | ZI (2.7 mm) | ZI (1.1 mm) | Low radical scavenger |
| VK, 5, 6 | No ZI | ZI decreased slightly (2.2 mm) | Significant decrease in ZI (0.7 mm) | ZI (2.7 mm) | ZI (1.1 mm) | Moderate radical scavenger |
| *R1, 7, 8 | No ZI | ZI decreased slightly (2.1 mm) | ZI is same as pyrogallol (1.2 mm) | ZI (2.7 mm) | ZI (1.1 mm) | Low radical scavenger |
| D, 9, 10 | No ZI | ZI is same as H2O2 (2.7 mm) | ZI is same as pyrogallol (1.2 mm) | ZI (2.7 mm) | ZI (1.1 mm) | No radical scavenger effect |
| RD, 11, 12 | No ZI | ZI decreased slightly (2.2 mm) | No ZI | ZI (2.7 mm) | ZI (1.1 mm) | Moderate radical scavenger |
| PR, 13, 14 | No ZI | No ZI | No ZI | ZI (2.7 mm) | ZI (1.1 mm) | High radical scavenger |

Figure 4:
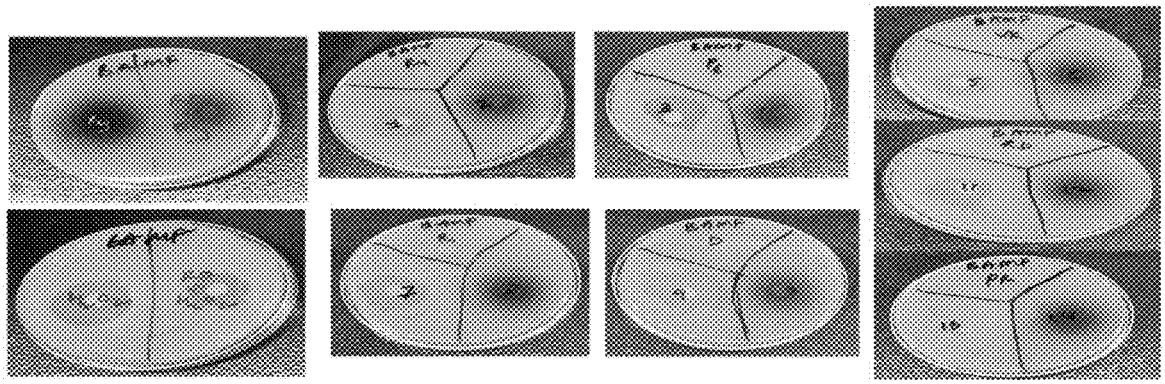
FIG. 4 is a series of images showing the zone of inhibition (ZI) for *Pseudomonas aeruginosa* (G−ve) in presence of pure H2O2, compound, Pyrogallol, (Compound+H2O2) and (Compound+Pyrogallol).

Decrease/Increase wrt pure H2O2 or pyrogallol. If ZI decreased (shrink) as compared to pyrogallol and H2O2, then they are providing antioxidant activity. See FIG. 4. R1 is a macrocycle which is showing low antioxidant activity but when complexed with D (i.e., RD) shows increased antioxidant activity. The drug itself shows no free radical scavenging effect in the presence of H2O2 and pyrogallol.

TABLE 4

Observations w.r.t. Zone of inhibition (ZI) for *klebsiella pneumoniae* (G -ve) bacteria

| Sample Code[a,b,c] | 5 uL of 0.01M Compound[a] | 5 uL of (Compound + H2O2)[b] | 5 uL of (Compound + Pyrogallol)[c] | 5 uL of 0.88M H2O2 | 5 uL of 1M pyrogallol | Inference |
|---|---|---|---|---|---|---|
| *R4, 1, 2 | No ZI | No ZI | No ZI | ZI (3 mm) | ZI (0.9 mm) | High OH radical scavenger |
| P6, 3, 4 | No ZI | ZI decreased slightly (2 mm) | No ZI | ZI (3 mm) | ZI (0.9 mm) | Moderate radical scavenger |
| VK, 5, 6 | No ZI | ZI decreased slightly (2.3 mm) | No ZI | ZI (3 mm) | ZI (0.9 mm) | Moderate radical scavenger |

TABLE 4-continued

Observations w.r.t. Zone of inhibition (ZI) for *klebsiella pneumoniae* (G -ve) bacteria

| Sample Code[a,b,c] | 5 uL of 0.01M Compound[a] | 5 uL of (Compound + H2O2)[b] | 5 uL of (Compound + Pyrogallol)[c] | 5 uL of 0.88M H2O2 | 5 uL of 1M pyrogallol | Inference |
|---|---|---|---|---|---|---|
| *R1, 7, 8 | No ZI | ZI decreased slightly (2.4 mm) | No ZI | ZI (3 mm) | ZI (0.9 mm) | Moderate radical scavenger |
| D, 9, 10 | No ZI | ZI decreased slightly (2.2 mm) | No ZI | ZI (3 mm) | ZI (0.9 mm) | Moderate radical scavenger |
| RD, 11, 12 | No ZI | ZI decreased slightly (2.2 mm) | No ZI | ZI (3 mm) | ZI (0.9 mm) | Moderate radical scavenger |
| PR, 13, 14 | No ZI | ZI decreased slightly (2.6 mm) | No ZI | ZI (3 mm) | ZI (0.9 mm) | Moderate radical scavenger |

Figure 5:
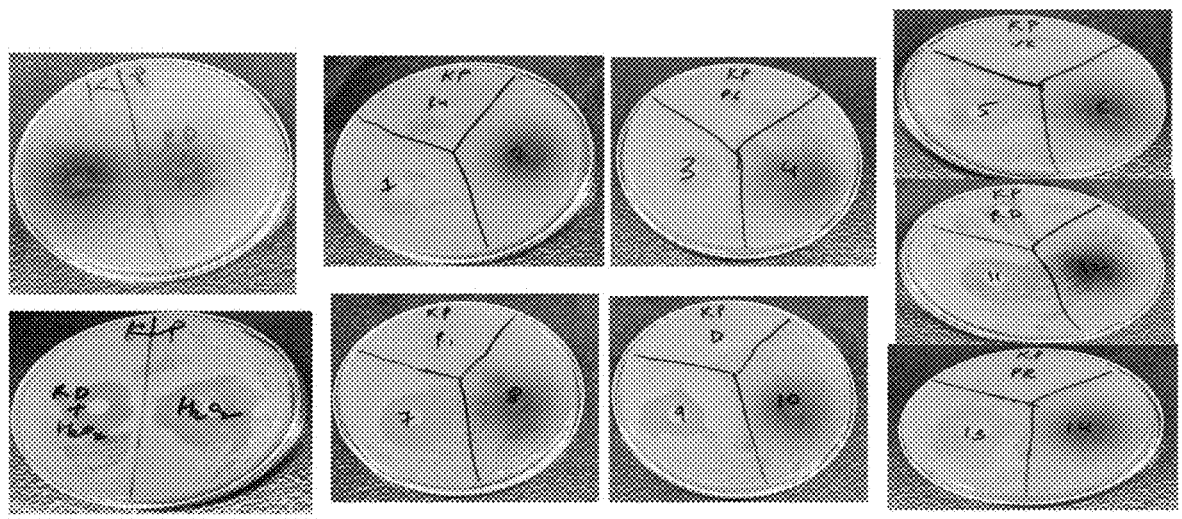
FIG. 5 is a series of images showing the zone of inhibition (ZI) for *Klebsiella pneumoniae* (G−ve) in presence of pure H2O2, compound, Pyrogallol, (Compound+H2O2) and (Compound+Pyrogallol).

Decrease/Increase wrt pure H2O2 or pyrogallol. If ZI decreased (shrink) as compared to pyrogallol and H2O2, then they are providing antioxidant activity. See FIG. 5.

TABLE 5

Observations w.r.t. Zone of inhibition (ZI) for *E. Coli* (G-ve) bacteria

| Sample Code[a,b,c] | 5 uL of 0.01M Compound[a] | 5 uL of (Compound + H2O2)[b] | 5 uL of (Compound + Pyrogallol)[c] | 5 uL of 0.88M H2O2 | 5 uL of 1M pyrogallol | Inference |
|---|---|---|---|---|---|---|
| *R4, 1, 2 | No ZI | Noticeable decrease ZI (1.7 mm) | No ZI | ZI (2.9 mm) | ZI (0.9 mm) | Moderate radical scavenger |
| P6, 3, 4 | No ZI | Noticeable decrease ZI (1.7 mm) | No ZI | ZI (2.9 mm) | ZI (0.9 mm) | Moderate radical scavenger |
| VK, 5, 6 | No ZI | No ZI | No ZI | ZI (2.9 mm) | ZI (0.9 mm) | High radical scavenger |
| *R1, 7, 8 | No ZI | Noticeable decrease ZI (1.9 mm) | No ZI | ZI (2.9 mm) | ZI (0.9 mm) | Moderate radical scavenger |
| D, 9, 10 | No ZI | Noticeable decrease ZI (1.7 mm) | No ZI | ZI (2.9 mm) | ZI (0.9 mm) | Moderate OH radical scavenger |
| RD, 11, 12 | No ZI | Significant decrease in ZI(1.1 mm) | No ZI | ZI (2.9 mm) | ZI (0.9 mm) | High radical scavenger |
| PR, 13, 14 | No ZI | Noticeable decrease ZI (2 mm) | No ZI | ZI (2.9 mm) | ZI (0.9 mm) | High OH radical scavenger |

Figure 6:
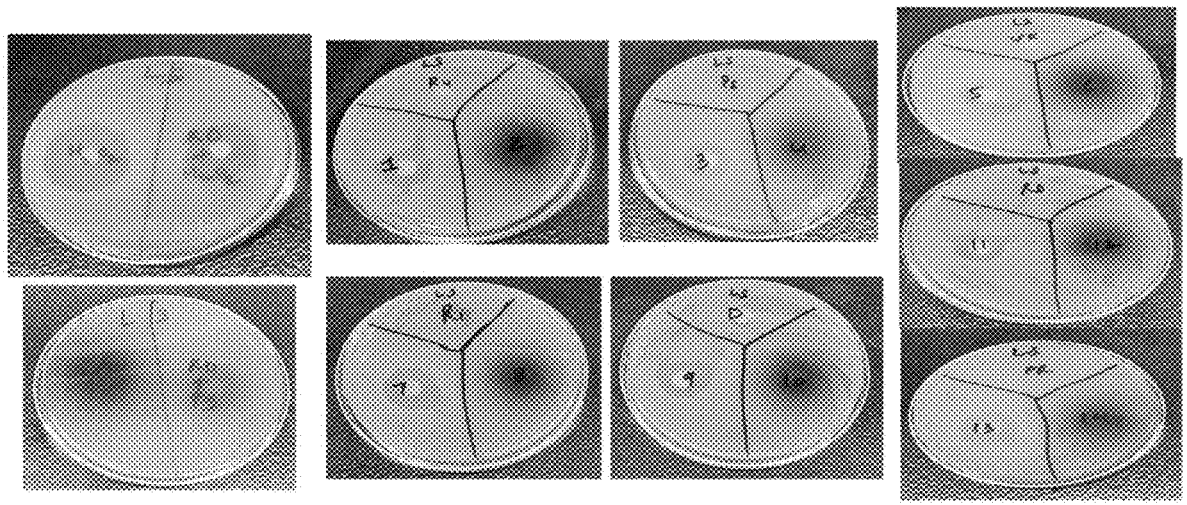
FIG. 6 is a series of images showing the zone of inhibition (ZI) for *E. Coli* (G–ve) in presence of pure H2O2, compound, Pyrogallol, (Compound+H2O2) and (Compound+Pyrogallol).

Decrease/Increase wrt pure H2O2 or pyrogallol. If ZI decreased (shrink) as compared to pyrogallol and H2O2, then they are providing antioxidant activity. See FIG. 6.

Example 4

Figure 10:
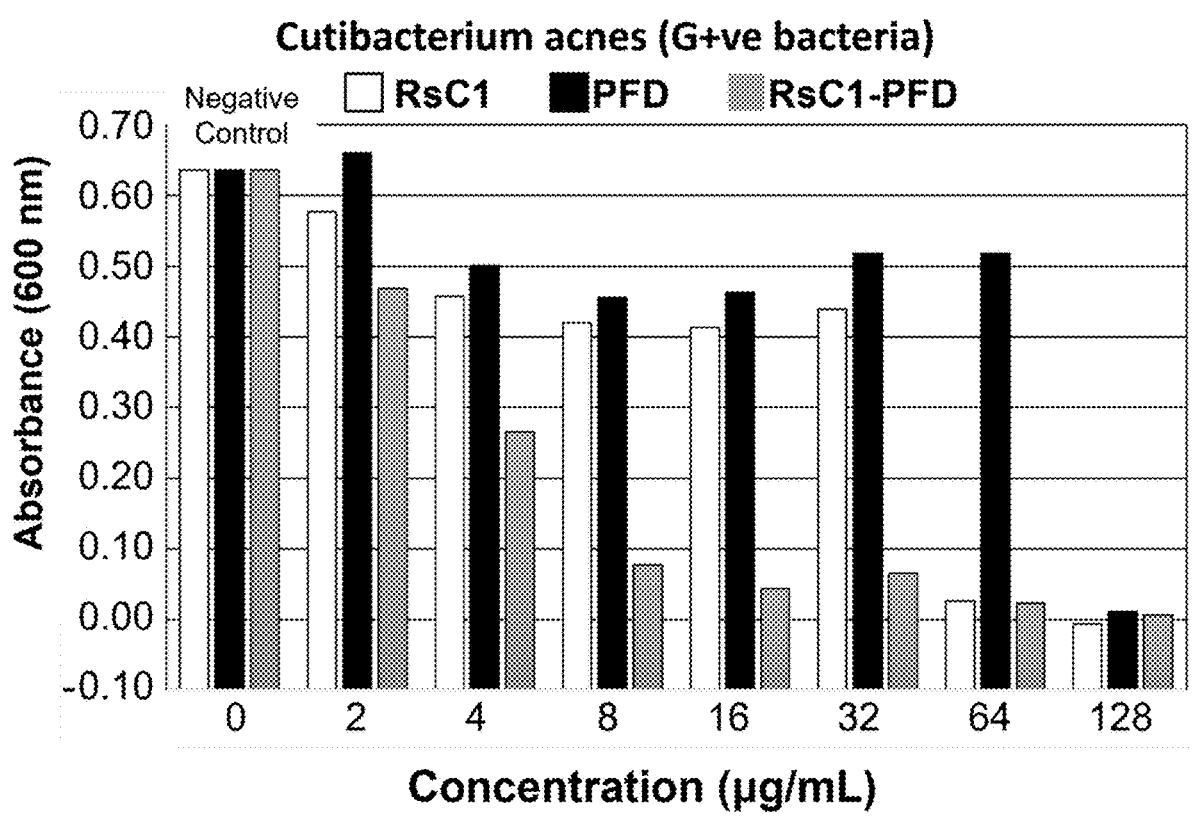
FIG. 10 is a bar plot showing the antibacterial activities of PFD, RsC1-PFD (1:1 complex), and RsC1 against a gram-positive anaerobic bacterial pathogen (*C. acnes*).

3 mg/ml stock solutions of RsC1, PFD and RsC1-PFD were prepared in DMSO (bcoz host soluble in DMSO solution). From the stock, a working solution 4× (highest conc. for each compound in plate) was prepared in LB media. 50 uL of LB media were first added in each well (96 well plate). Then a 4× solution of each respective compound was added to the first row (A4-A12) except A1-A3 (Positive control/bacterial innoculum). Then the 4× was serially diluted up to well G for all 3 compounds. (A-G). Then, a 50 uL aliquot of the 100-fold diluted bacterial inoculum was added in each test well. Individual test concentrations (in triplicate wells in a 96-well plate) for the given compounds were achieved by serial dilution by using LB medium. Total volume in each well was 100 uL. The final-test concentration range for the individual test compounds for *C. acne* were as follows: Macrocycle, PFD and RsC1-PFD complex (128-2 ug/mL). The results are shown in FIG. 10, which is a bar plot of absorbance (at 600 nm) at various test compound concentrations, showing the percent inhibition of pathogen growth in the presence of decreasing concentrations of the test compounds using a twofold dilution series. RsC1-PFD showed inhibition at 16 µg/mL, whereas RsC1 alone only showed 35% inhibition at the same concentration.

Example 5

Figure 11:
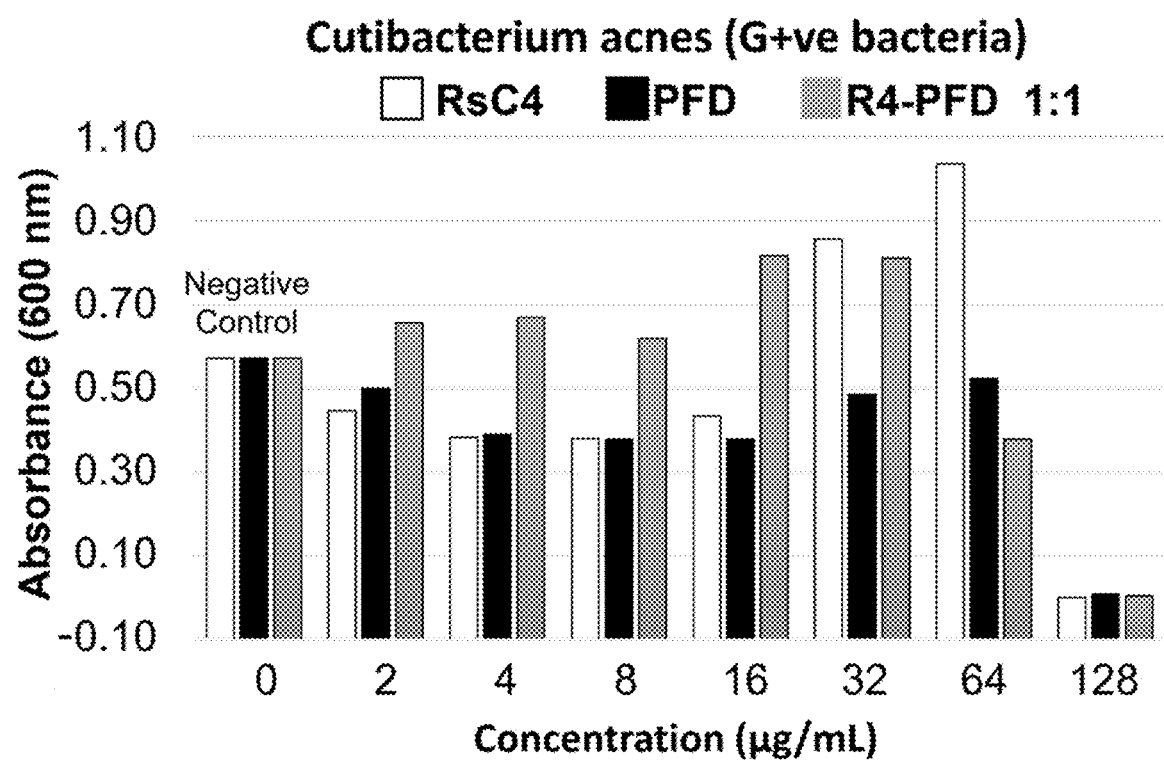
FIG. 11 is a bar plot showing the antibacterial activities of PFD, RsC4-PFD (1:1 complex), and RsC4 against a gram-positive anaerobic bacterial pathogen (*C. acnes*).

3 mg/ml stock solutions of PFD, RsC4-PFD (1:1 complex), and RsC4 were prepared in DMSO (bcoz host soluble in DMSO solution). From the stock, a working solution 4× (highest conc. for each compound in plate) was prepared in LB media. 50 uL of LB media were first added in each well (96 well plate). Then a 4× solution of the respective compound was added to the first row (A4-A12) except A1-A3 (Positive control/bacterial innoculum). Then, the 4× was serially diluted up to well G for all 3 compounds. (A-G). Then, a 50 uL aliquot of the 100-fold diluted bacterial inoculum was added in each test well. Individual test concentrations (in triplicate wells in a 96-well plate) for the given compounds were achieved by serial dilution by using LB medium. Total volume in each well is 100 uL. The final-test concentration range for the individual test compounds for *C. acne* as follows: Macrocycle, PFD and RsC4-PFD complex (128-2 ug/mL). The results are shown in FIG. 11.

Example 6

3 mg/ml stock solutions of PFD, RsC1, RsC1-PFD (1:1 complex), RsC4, and RsC4-PFD (1:1 complex) were prepared in DMSO (bcoz host soluble in DMSO solution). From the stock, a working solution 4× (highest conc. for each compound in plate) was prepared in LB media. 50 uL of LB media was first added in each well (96 well plate). Then a 4× solution of the respective compound was added to the first row (A4-A12) except A1-A3 (Positive control/bacterial innoculum). Then, the 4× was serially diluted up to well G for all 3 compounds. (A-G). Then, a 50 uL aliquot of the 100-fold diluted bacterial inoculum was added in each test well. Individual test concentrations (in triplicate wells in a 96-well plate) for the given compounds were achieved by serial dilution by using LB medium. Total volume in each well is 100 uL. The final-test concentration range for the individual test compounds for *C. acnes, S. aureus* and *P. aeruginosa* are as follows: PFD, RsC1, RsC4, RsC1-PFD complex and RsC4-PFD complex (128-2 ug/mL). The results are shown in Table 6.

TABLE 6

Antibacterial activities of cocrystals and their individual components

| Test compound | MIC (μg/mL); GI (%) | | |
|---|---|---|---|
| | *S. aureus* (MU50) | *P. aeruginosa* (BAMF) | *C. acnes* |
| PFD | 128; 45 | 128; 35 | 128; 98 |
| RsC$_1$ | 16; 98 | 64; 47 | 64; 96 |
| RsC$_1$-PFD (1) | 8; 99 | 128; 43 | 16; 93 |
| RsC$_4$ | 128; 52 | 64; 56 | 128; 98 |
| RsC$_4$-PFD (2) | 128; 26 | 128; 39 | 128; 99 |

*C. acnes: Cutibacterium acnes*;
*S. aureus: Staphylococcus aureus*;
*P. aeruginosa: Pseudomonas aeruginosa*;
MIC: Minimum inhibitory concentration;
GI: Growth inhibition.
PFD: pirfenidone;
RsC$_1$: C-methylresorcin[4]arene;
1:1 cocrystal of RsC1-PFD (1);
RsC$_4$: C-butylresorcin[4]arene;
1:1 cocrystal of RsC4-PFD (2).

Figure 1B:
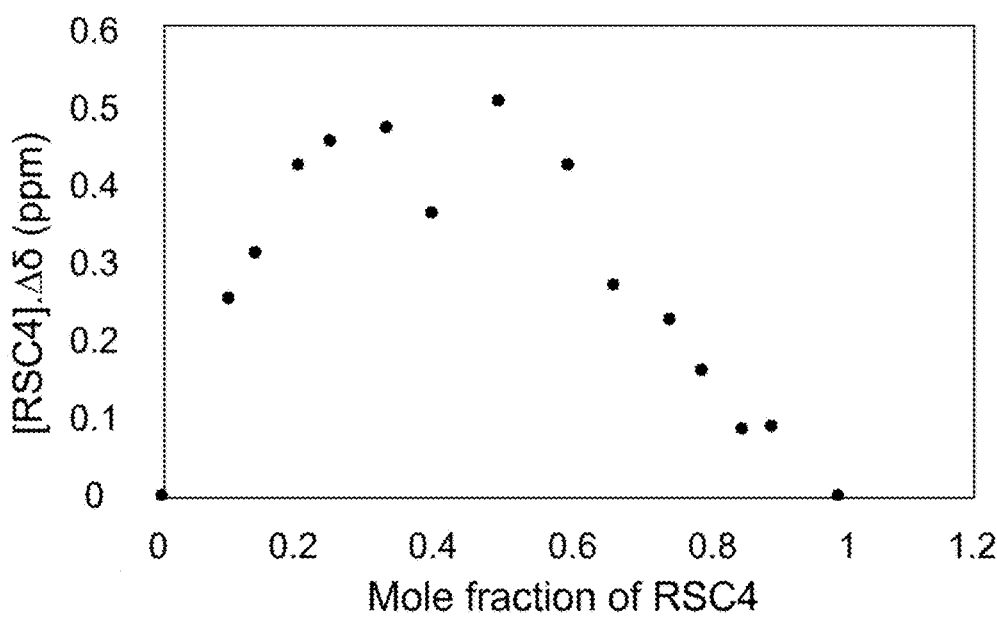
FIG. 1B is a graph showing a Job's plot constructed from the chemical shift change ($\Delta\delta$) of the aromatic protons (#C) of RsC4 in 1H NMR spectra by varying the ratio between PFD and RsC4.

FIG. 1A shows a Job's plot constructed from the chemical shift change (Δδ) of the phenyl ring protons (#2) of PFD in 1H NMR spectra by varying the ratio between PFD and RsC4. FIG. 1B shows a Job's plot constructed from the chemical shift change (Δδ) of the aromatic protons (#C) of RsC4 in 1H NMR spectra by varying the ratio between PFD and RsC4.

Diffusion coefficient of PFD in equimolar mixture has changed drastically compared to PFD alone (above spectra, FIGS. 1A and 1B) which indicates the PFD bind to RsC4 in the mixture and diffuses at slower rate compared to PFD alone. The interaction between host and guest were loose/weak, therefore RsC4 and PFD peaks do not correspond to the same diffusion constant and have different position on the y axis. The diffusion coefficient of solvent ACN-d3 is 3.17×10-9. The broad, mobile OH proton at 7.7 ppm of host RsC4 has disappeared in the spectra. The y-axis is shown as log D.

Figure 7:
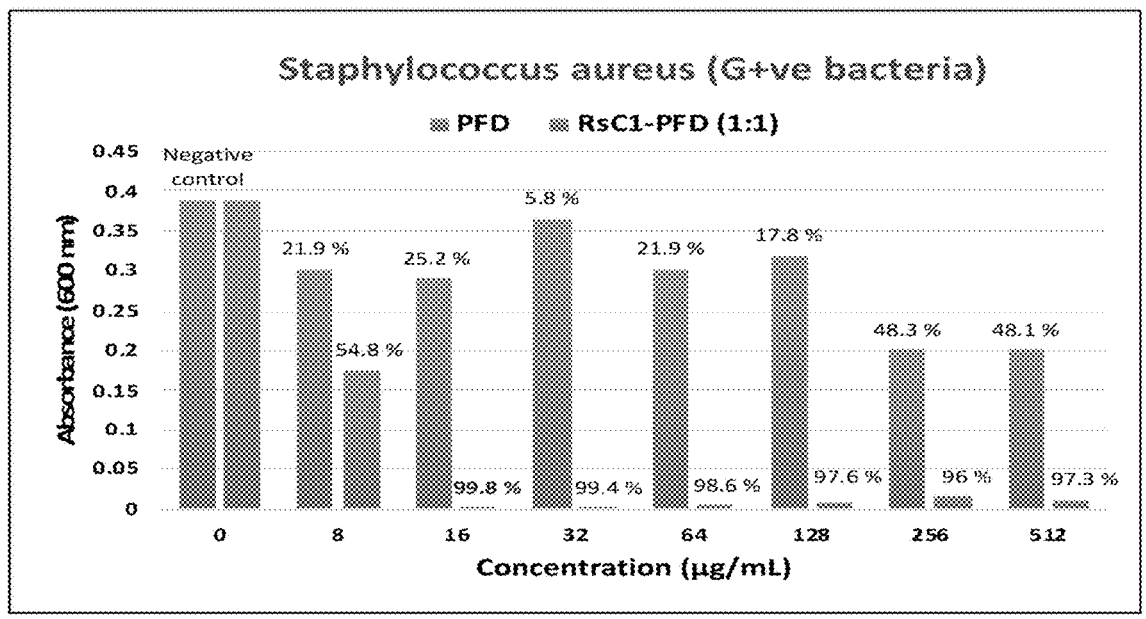
FIG. 7 is a graph showing the antibacterial activity of PFD alone and RsC1-PFD complex against *S. aureus*. The percent on each bar indicates growth inhibition at a specific concentration (minimum inhibitory concentration).
Figure 8:
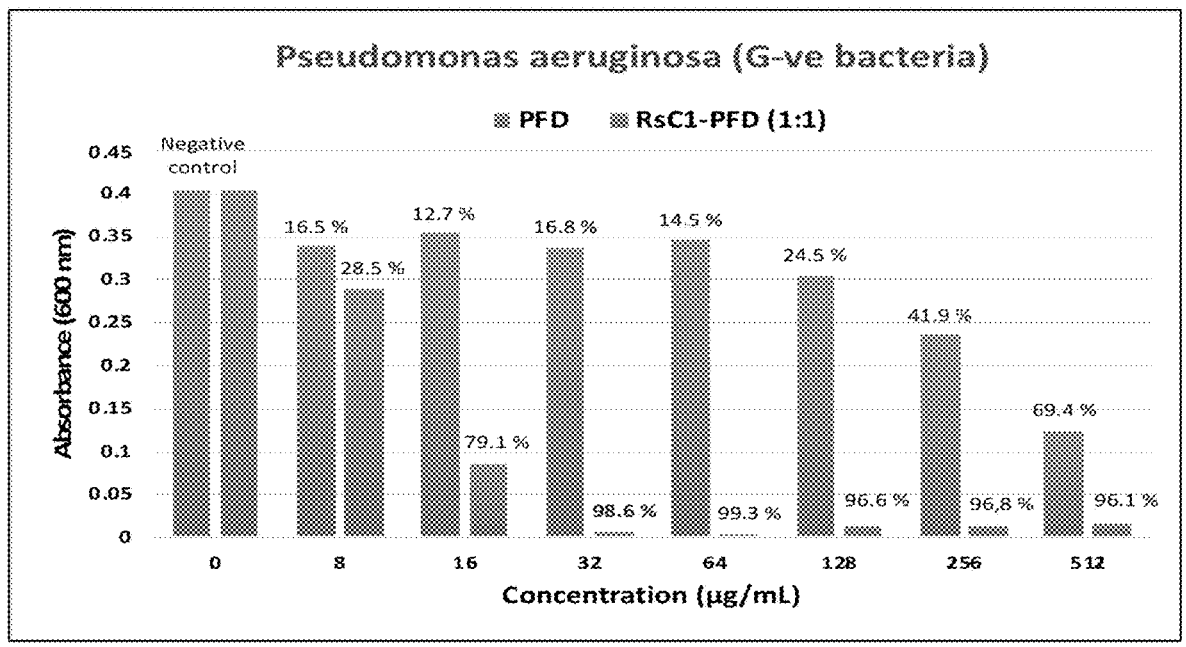
FIG. 8 is a graph showing the antibacterial activity of PFD alone and RsC1-PFD complex against *P. aeruginosa*. The percent on each bar indicates growth inhibition at a specific concentration (minimum inhibitory concentration).
Figure 9:
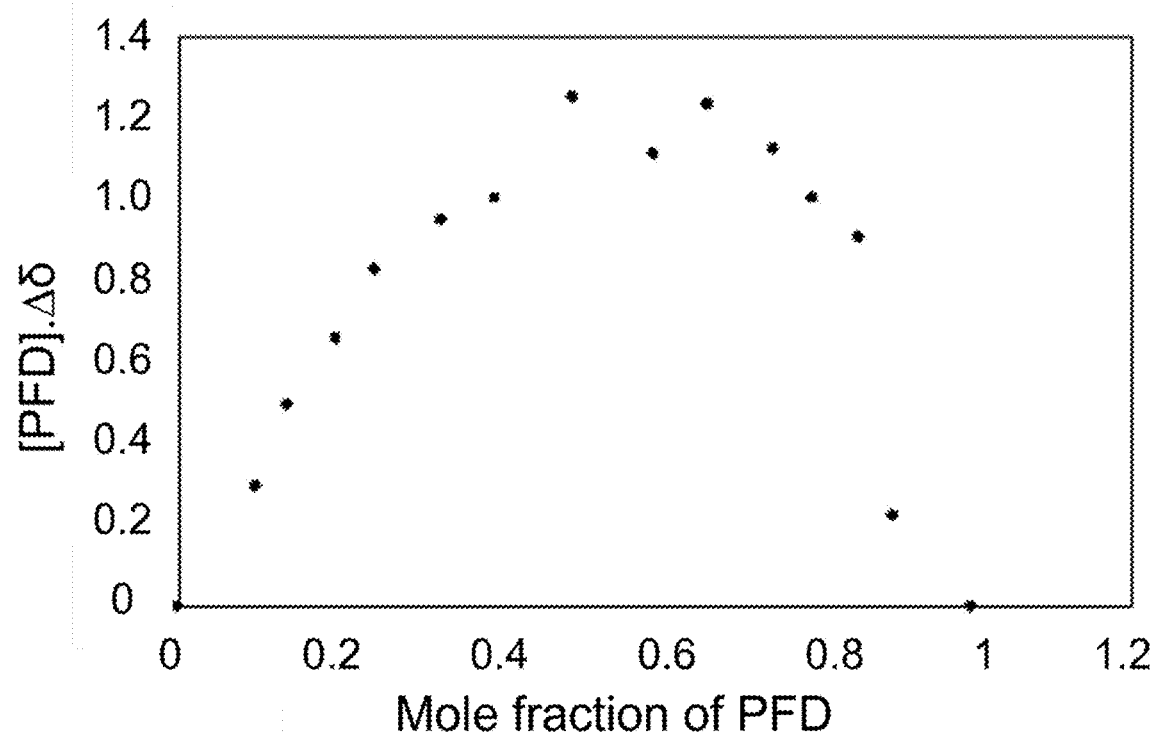
FIG. 9 is a Job's plot (NMR titration), Stoichiometry 1:1.

FIG. 7 is a graph showing the antibacterial activity of PFD alone and RsC1-PFD complex against *S. aureus*. The percent on each bar indicates growth inhibition at a specific concentration (minimum inhibitory concentration). FIG. 8 is a graph showing the antibacterial activity of PFD alone and RsC1-PFD complex against *P. aeruginosa*. The percent on each bar indicates growth inhibition at a specific concentration (minimum inhibitory concentration). FIG. 9 is a Job's plot (NMR titration), Stoichiometry 1:1.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A composition comprising a cocrystal complex of pirfenidone with a polyphenolic macrocycle host.

2. The composition of claim 1 wherein the macrocycle is calixarene or a calixarene derivative.

3. The composition of claim 2 wherein the calixarene derivative is resorcin[4]arene.

4. The composition of claim 3 wherein the resorcin[4]arene is C-methylresorcin[4]arene (RsC1).

5. The composition of claim 3 wherein the resorcin[4]arene is C-butylresorcin[4]arene (RsC4).

6. The composition of claim 1 wherein the cocrystal complex comprises pirfenidone with a resorcin[4]arene macrocycle with two different tail lengths.

7. An antibacterial composition comprising the cocrystal complex of claim 2.

8. The antibacterial composition of claim 7, wherein the cocrystal complex comprises from about 4 to about 8% by weight of the composition.

9. The antibacterial composition of claim 7, wherein the cocrystal complex comprises from about 2 to about 10% by weight of the composition.

10. The antibacterial composition of claim 7, further comprising a cosmetically acceptable carrier.

11. The antibacterial composition of claim 10, wherein said carrier comprises one or more carriers selected from the group consisting of preservatives, emollients, emulsifying agents, surfactants, moisturizers, gelling agents, thickening agents, conditioning agents, film-forming agents, stabilizing agents, anti-oxidants, texturizing agents, gloss agents, mattifying agents, solubilizers, pigments, dyes, and fragrances.

12. A method of treating a subject to prevent, treat or reverse acne or post-acne lesions comprising applying a therapeutically effective amount of the composition of claim 1 to the skin of a subject in need of such treatment.

13. The method of claim 12 wherein a therapeutically effective amount of a cocrystal complex of pirfenidone with a resorcin[4]arene is applied to the skin of a subject in need of such treatment.

14. The method of claim 12 wherein a therapeutically effective amount of a cocrystal complex of pirfenidone with C-methylresorcin[4]arene is applied to the skin of a subject in need of such treatment.

15. The method of claim 12 wherein a therapeutically effective amount of a cocrystal complex of pirfenidone with C-butylresorcin[4]arene is applied to the skin of a subject in need of such treatment.

\* \* \* \* \*